United States Patent
Aranda-Martinez et al.

(10) Patent No.: US 7,132,549 B2
(45) Date of Patent: Nov. 7, 2006

(54) PROCESS

(75) Inventors: Julian Aranda-Martinez, Freiburg (DE); Catherine Dunne, Sandwich (GB); Juergen Friedrich Kleinschroth, Freiburg (DE); Julie Ann MacRae, Sandwich (GB); Richard Anthony Storey, Sandwich (GB); Ellen Johanna Weilbacher, Freiburg (DE)

(73) Assignee: Pfizer Inc., New York, NY (US)

( * ) Notice: Subject to any disclaimer, the term of this patent is extended or adjusted under 35 U.S.C. 154(b) by 246 days.

(21) Appl. No.: 10/852,038

(22) Filed: May 24, 2004

(65) Prior Publication Data

US 2005/0032872 A1     Feb. 10, 2005

Related U.S. Application Data

(60) Provisional application No. 60/489,829, filed on Jul. 23, 2003.

(30) Foreign Application Priority Data

May 30, 2003    (GB)    ................... 0312478.1

(51) Int. Cl.
*C07D 209/02*     (2006.01)

(52) U.S. Cl. ...................................................... 548/465

(58) Field of Classification Search ................. 548/465
See application file for complete search history.

(56) References Cited

U.S. PATENT DOCUMENTS 5,607,951 A     3/1997   Macor et al.

FOREIGN PATENT DOCUMENTS

| WO | WO 9206973 | 4/1992 |
|---|---|---|
| WO | WO 96/06842 | 3/1996 |
| WO | WO 99/01135 | 1/1999 |
| WO | WO 01/23377 A2 | 4/2001 |

*Primary Examiner*—Kamal A. Saeed
*Assistant Examiner*—Robert Shiao
(74) *Attorney, Agent, or Firm*—Charles W. Ashbrook; David R. Kurlandsky

(57) ABSTRACT

The present invention provides an improved process for the preparation of a polymorph of eletriptan hemisulphate.

10 Claims, 10 Drawing Sheets

PROCESS

This application is a United States utility application, which claims the benefit of priority to United Kingdom patent application Serial No. 0312478.1 filed May 30, 2003 and U.S. provisional application Ser. No. 60/489,829 filed Jul. 23, 2003.

The present invention relates to an improved process for the preparation of a particular crystalline form of eletriptan hemisulphate.

Eletriptan, 3-{[1-methylpyrrolidin-2(R)-yl]methyl}-5-(2-phenylsulfonylethyl)-1H-indole, and a process for its manufacture, are disclosed in U.S. Pat. No. 5,607,951.

Eletriptan hemisulphate has the structure of formula (I) below.

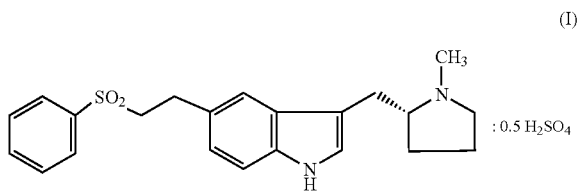

International patent application number PCT/EP95/01914, published as WO-A-96/06842, discloses two crystalline forms of eletriptan hemisulphate. The first, designated the α-form, is characterised as having a melting point of 185° C. This form will be referred to below as eletriptan hemisulphate form II. The second, designated the β-form, is characterised as having a melting point of 145–147° C. and will be referred to below as eletriptan hemisulphate form III.

International patent application number PCT/EP98/04176, published as WO-A-99/01135, describes a process for making eletriptan hemisulphate form III. International patent application number PCT/IB00/01305, published as WO-A-01/23377, discloses a further crystalline form of eletriptan hemisulphate. This polymorph, which will be referred to below as eletriptan hemisulphate form I, is characterised by its DSC melting point of 226° C. and other data such as its powder X-ray diffraction (PXRD) pattern. Also disclosed are several processes for preparing eletriptan hemisulphate form I, both from eletriptan itself and from eletriptan hemisulphate of mixed morphology (i.e. existing at least partly in one or more other polymorphic forms). In the latter case, the hemisulphate salt of mixed morphology is slurried in refluxing tetrahydrofuran (THF), ethanol, isopropanol or industrial methylated spirit (IMS) and then filtered, washed and dried to yield eletriptan hemisulphate form I.

These processes for preparing eletriptan hemisulphate form I have proven to be unsatisfactory, especially on a large scale, and do not give the form I polymorph reliably. For instance, in the case where THF is used as the solvent, the product is often obtained contaminated with solvated/hydrated forms (particularly hydrates). Such undesired forms are obtained in an unpredictable fashion.

It will be appreciated that in the large scale preparation of a drug molecule it is essential to establish a process that is robust in the sense of reliably producing a homogeneous product containing the same crystalline form, free of other crystalline forms and solvates.

There is thus a need to provide a high-yielding and robust process for the preparation of eletriptan hemisulphate form I which can be carried out reliably on a large scale.

Figure 1A:
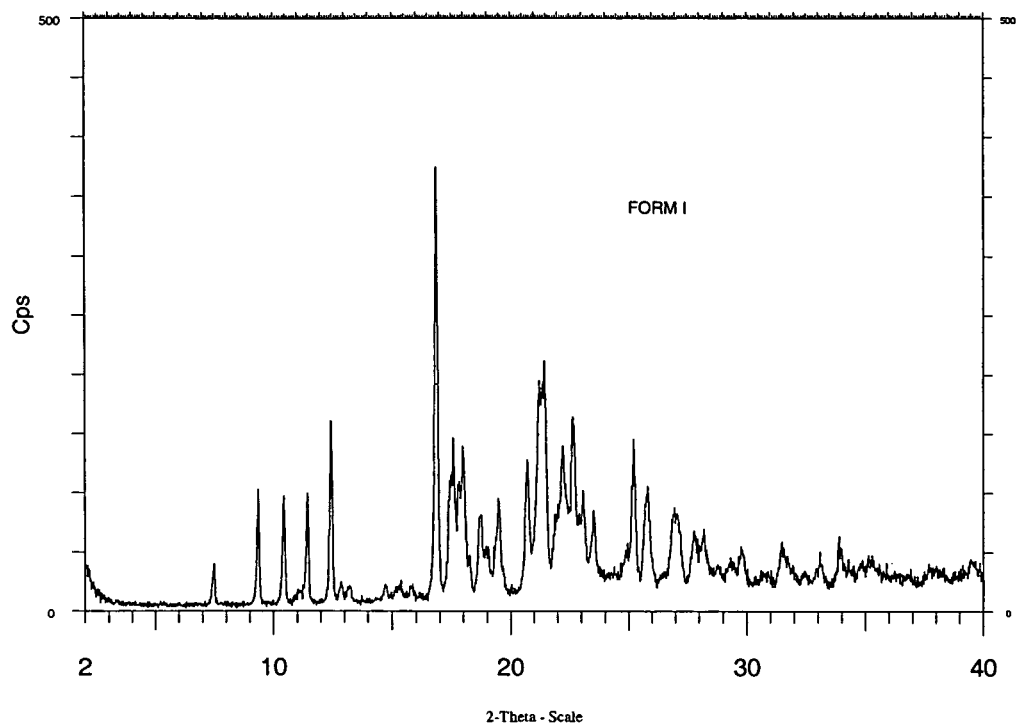
FIG. 1a illustrates a powder x-ray diffraction (PXRD) pattern of Form I of eletriptan hemisulphate and FIG. 1b illustrates the differential scanning calorimetry (DSC) thermogram of Form I.

It has now been surprisingly found that it is possible to prepare eletriptan hemisulphate form I in a reliable and high-yielding manner. In the new process, a stirred suspension of any other form of eletriptan hemisulphate (or any mixture of forms) in a $C_1$–$C_6$ alkyl acetate solvent is heated and then concentrated by azeotropic distillation prior to recovery of the product.

A $C_1$–$C_6$ alkyl acetate is a compound of the formula $CH_3COOR$, wherein R is a $C_1$–$C_6$ alkyl group. Preferred solvents are ethyl acetate and n-propyl acetate. Ethyl acetate is particularly preferred.

The volume of solvent used, in relation to the weight of eletriptan hemisulphate, is not determinative of success. Where ethyl acetate is used as the solvent, an amount of from 8 to 12 liters of ethyl acetate per kilogram of eletriptan hemisulphate is preferably employed.

However, the amount of water present in the reaction is crucial to the success of the process and must be no more than 3% volume/volume. In the case where the hemisulphate starting material is hydrated, the amount of bound water present must be calculated [Karl Fischer (KF) analysis is the most convenient analytical tool] and taken into consideration. If necessary, the starting material can be dried to reduce its water content. The water content of the reaction mixture is preferably from 0.2 to 2% volume/volume, most preferably from 1.3 to 2% volume/volume.

In general, those forms of eletriptan that are less resistant to conversion, having a low crystallinity, can be easily converted in a reaction mixture having a lower water content whilst more resistant batches are more conveniently converted in a reaction mixture having a higher water content.

The heating should be continued until all the hemisulphate salt present has been converted into the form I polymorph. This will typically take several hours, usually from 4 to 24 hours. The conversion time will depend on the temperature selected, a higher temperature resulting in a lower conversion time. Preferably, the slurry is heated at from 60 to 80° C. Most preferably, when ethyl acetate is chosen as the solvent, the slurry is heated under reflux. The reaction mixture may also be pressurised to increase the rate of conversion. Differential scanning calorimetry (DSC), performed on a sample taken from the reaction mixture, can be used as a crude indication of how far the conversion has progressed.

When the conversion is complete, a portion of the solvent must, if necessary, be removed by azeotropic distillation until the water content of the reaction mixture has fallen to below 1% volume/volume. This step is important in order to avoid the later formation of any solvates of the product at ambient temperature. For instance, where about 10 liters of ethyl acetate per kg of eletriptan hemisulphate starting material has been used, it is usually sufficient to distil off from one to two fifths of the volume added.

Occasionally, if the conversion is slow, it is advantageous to carry out the azeotropic distillation during the conversion rather than after the conversion. In this case, the water content of the reaction mixture should be reduced to below 0.3% volume/volume, fresh, dry solvent should be added and the reaction should be heated under reflux for a further period.

The product can be recovered by filtration. Typically, the reaction mixture is cooled to from 20 to 25° C., filtered, washed with solvent (preferably about 1 liter per kilogram of product) and dried (preferably at 70° C. in vacuo). De-lumping may be necessary in certain instances.

The average yield of eletriptan hemisulphate form I is 94%.

In principle, the starting material for the conversion may be amorphous eletriptan hemisulphate, any single polymorphic form of eletriptan hemisulphate, any hydrated/solvated form of either or any mixture of the forgoing, including mixtures comprising form I itself.

The polymorphic forms of eletriptan hemisulphate that are known are listed below along with characterising data. Polymorphic forms I–XI are known as well as two ethyl acetate solvates XII and XIII and an n-propyl acetate solvate XIV, these solvates containing varying amounts of water. The solvates are readily observed on slurrying amorphous eletriptan hemisulphate in either ethyl acetate or n-propyl acetate, respectively. Form IV is observed when a solution of eletriptan in acetonitrile is treated with dilute sulphuric acid.

Powder X-ray diffraction (PXRD) patterns were typically determined using a SIEMENS D5000 powder X-ray diffractometer fitted with an automatic sample changer, a theta-theta goniometer, automatic beam divergence slits, a secondary monochromator and a scintillation counter. The samples were prepared for analysis by packing the powder on to silicon wafer specimen mounts. Each specimen was rotated whilst being irradiated with copper K-alpha$_1$ X-rays (wavelength=1.5406 Å) with the X-ray tube operated at 40 kV/40 mA. The analyses were typically performed with the goniometer running in continuous mode set for a 5 second count per 0.02° step over a two theta range of 2° to 40°. Differential scanning calorimetry (DSC) was performed using a Perkin Elmer Diamond DSC instrument fitted with an automatic sample changer. Approximately 3 mg of each sample was accurately weighed into a 50 microliter aluminium pan and crimp sealed with a perforated lid. The samples were heated at 20° C./minute over the range 30° C. to 250° C. with a nitrogen gas purge. DSC thermograms for forms III and above have a similar profile with dehydration or desolvation and melt up to ~140° C. then a exothermic recrystallisation event to Form II (Peak at about 186° C.) and then a second exothermic recrystallisation event to Form I (Peak at about 226° C.).

FORM I
PXRD See FIG. 1a
The characteristic peaks are:

| 2-Theta ° | Intensity % | 2-Theta ° | Intensity % | 2-Theta ° | Intensity % |
|---|---|---|---|---|---|
| 7.341 | 8.9 | 20.649 | 34.2 | 27.773 | 18 |
| 9.234 | 27.4 | 21.256 | 49.6 | 28.139 | 16.9 |
| 10.327 | 25.6 | 21.894 | 21.5 | 28.759 | 10.3 |
| 11.315 | 26.5 | 22.162 | 37.3 | 29.262 | 11.9 |
| 12.351 | 42.7 | 22.613 | 43.9 | 29.748 | 13.7 |
| 12.777 | 6.3 | 23.027 | 27 | 30.643 | 8.7 |
| 16.791 | 100 | 23.452 | 22.6 | 31.472 | 15.4 |
| 17.478 | 38.9 | 24.849 | 13.6 | 32.423 | 8.9 |
| 17.928 | 37.2 | 25.169 | 38.6 | 33.089 | 10.2 |
| 18.651 | 21.4 | 25.738 | 26.8 | 33.889 | 16.4 |
| 18.92 | 14.5 | 26.899 | 23.2 | 34.804 | 10.6 |
| 19.43 | 25.3 | | | | |

Figure 1B:
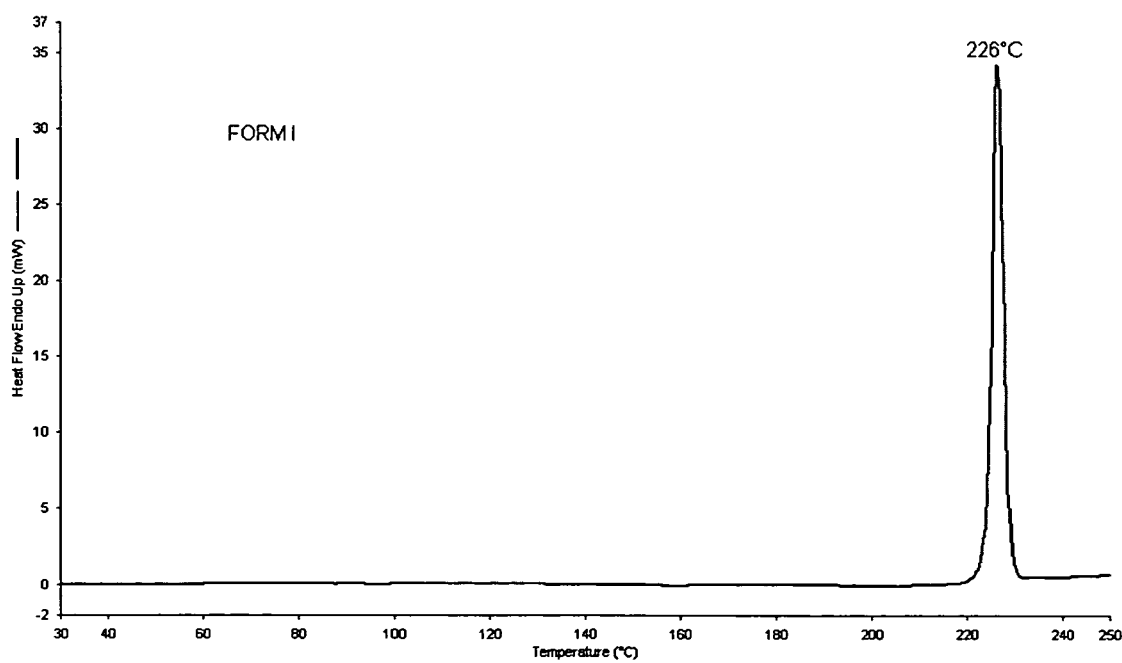

DSC See FIG. 1b (226° C., endotherm).

Figure 2:
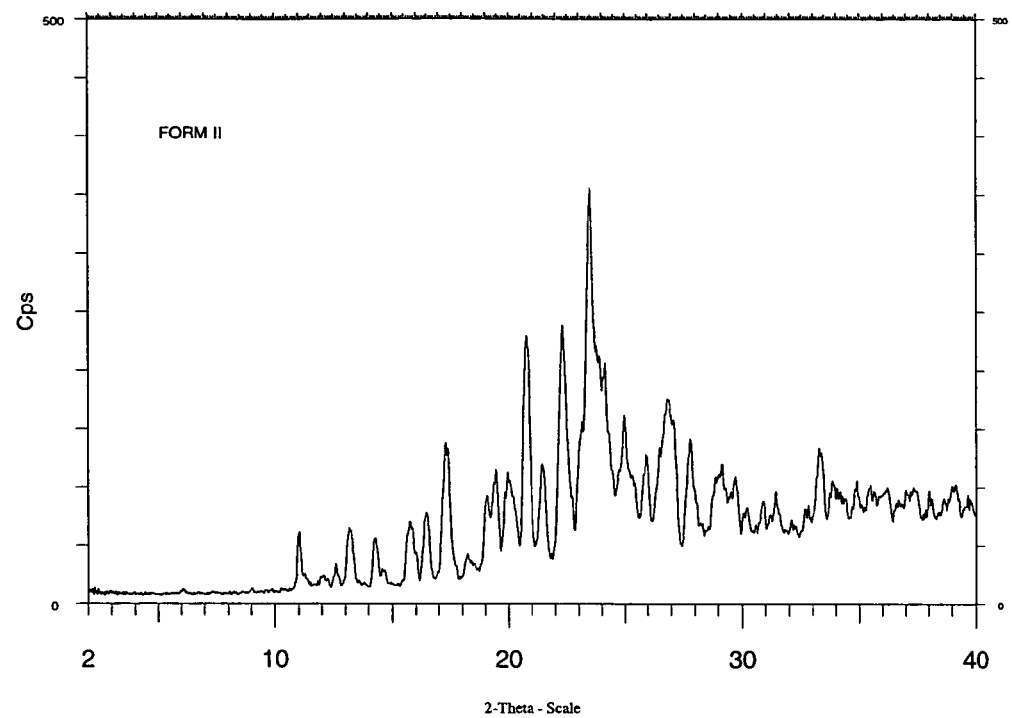
FIG. 2 illustrates the PXRD patterns of Form II of eletriptan hemisulphate.

FORM II
PXRD See FIG. 2
The characteristic peaks are:

| 2-Theta ° | Intensity % | 2-Theta ° | Intensity % | 2-Theta ° | Intensity % |
|---|---|---|---|---|---|
| 10.974 | 17 | 21.456 | 33.4 | 28.966 | 29.9 |
| 12.566 | 9.3 | 22.297 | 67 | 29.164 | 33.6 |
| 13.142 | 18.1 | 23.104 | 43.5 | 29.72 | 30.4 |
| 14.239 | 15.5 | 23.477 | 100 | 30.207 | 23 |
| 14.596 | 7.6 | 23.834 | 60.6 | 30.918 | 24.6 |
| 15.737 | 19.6 | 24.113 | 56.4 | 31.223 | 21.9 |
| 15.942 | 12.5 | 24.978 | 45.4 | 31.465 | 26.9 |
| 16.44 | 21.7 | 25.344 | 30.7 | 32.117 | 20.1 |
| 17.315 | 37.7 | 25.95 | 35.8 | 32.752 | 21.7 |
| 18.191 | 11.8 | 26.545 | 37.5 | 33.354 | 37.4 |
| 19.054 | 25.9 | 26.877 | 49 | 33.923 | 29 |
| 19.429 | 32.2 | 27.07 | 43.7 | 34.414 | 25.1 |
| 19.979 | 30.7 | 27.818 | 39.6 | 34.898 | 29.4 |
| 20.758 | 64.5 | | | | |

DSC 186° C., endotherm.

Figure 3A:
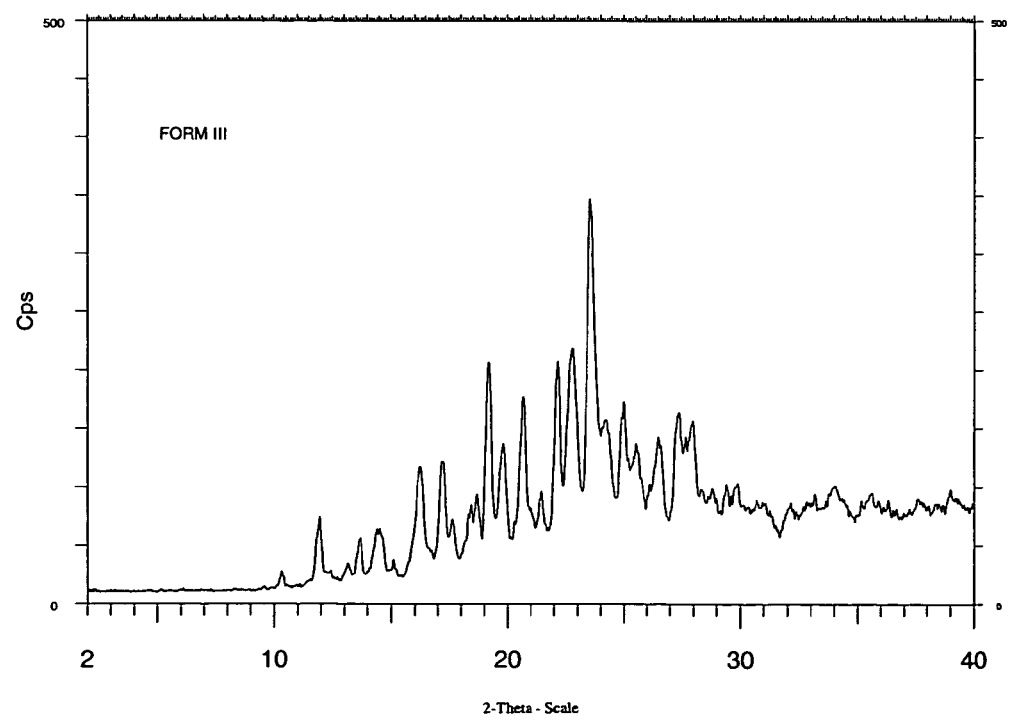
FIG. 3a illustrates the PXRD patterns of Form III of eletriptan hemisulphate and FIG. 3b illustrates the DSC thermogram of Form II for eletriptan hemisulphate.

FORM III
PXRD See FIG. 3a
The characteristic peaks are:

| 2-Theta ° | Intensity % | 2-Theta ° | Intensity % | 2-Theta ° | Intensity % |
|---|---|---|---|---|---|
| 10.24 | 7.9 | 19.141 | 59.5 | 26.493 | 41 |
| 11.858 | 21.3 | 19.76 | 39.3 | 27.335 | 47 |
| 13.077 | 9.7 | 20.623 | 50.9 | 27.637 | 41.8 |
| 13.6 | 15.6 | 21.408 | 27.5 | 27.923 | 44.5 |
| 14.47 | 18.2 | 22.104 | 59.6 | 28.357 | 28.1 |
| 15.035 | 10.7 | 22.715 | 63 | 28.82 | 28.3 |
| 16.171 | 33.5 | 23.515 | 100 | 29.405 | 29.2 |
| 17.138 | 34.8 | 24.166 | 45.2 | 29.826 | 28.9 |
| 17.558 | 20.5 | 24.943 | 49.8 | 32.094 | 24.7 |
| 18.344 | 24.2 | 25.508 | 38.9 | 34.021 | 28.8 |
| 18.63 | 26.8 | | | | |

Figure 3B:
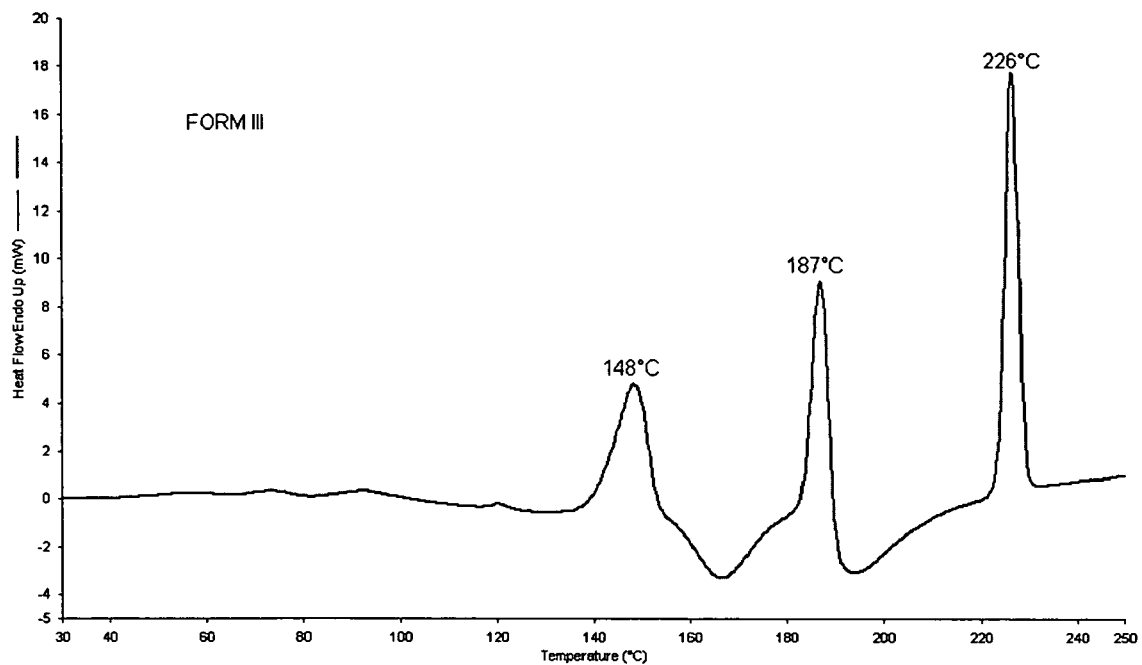

DSC See FIG. 3b (148° C., 187° C., 226° C., all endotherm).

Figure 4:
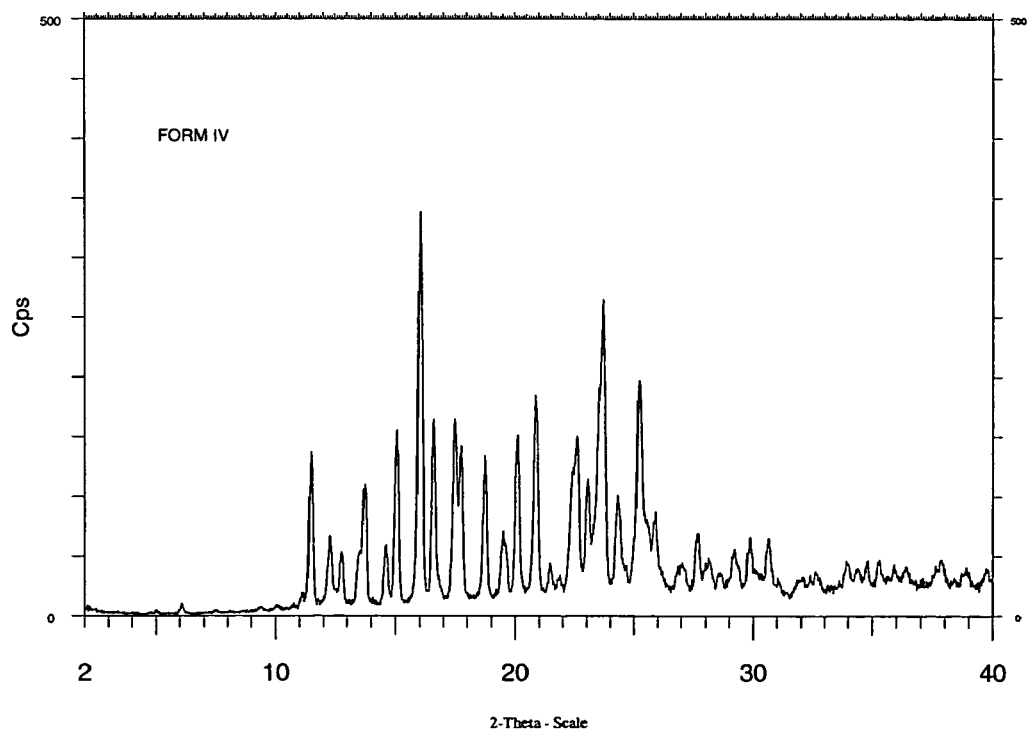
FIG. 4 illustrates the PXRD patters of Form IV for eletriptan hemisulphate.

FORM IV
PXRD See FIG. 4
The characteristic peaks are:

-continued

| 2-Theta ° | % | 2-Theta ° | % | 2-Theta ° | Intensity % |
|---|---|---|---|---|---|
| 11.445 | 40.3 | 19.505 | 20.7 | 25.883 | 24 |
| 12.245 | 19.4 | 20.093 | 44.5 | 26.919 | 11.7 |
| 12.739 | 15.6 | 20.845 | 54.5 | 27.672 | 20.2 |
| 13.436 | 14.9 | 21.471 | 12.8 | 28.161 | 14.1 |
| 13.693 | 32.1 | 21.847 | 9.1 | 28.615 | 10.4 |
| 14.586 | 17.3 | 22.417 | 35.3 | 29.222 | 16 |
| 15.026 | 45.6 | 22.597 | 44.3 | 29.881 | 19 |
| 15.998 | 100 | 23.027 | 33.5 | 30.652 | 18.9 |
| 16.543 | 48.3 | 23.517 | 56.3 | 32.671 | 10.2 |
| 17.457 | 48.4 | 23.692 | 78.3 | 34 | 12.7 |
| 17.711 | 41.8 | 24.327 | 29.7 | 34.4 | 11.6 |
| 18.716 | 39.3 | 25.223 | 58.2 | 34.805 | 13.1 |

Figure 5A:
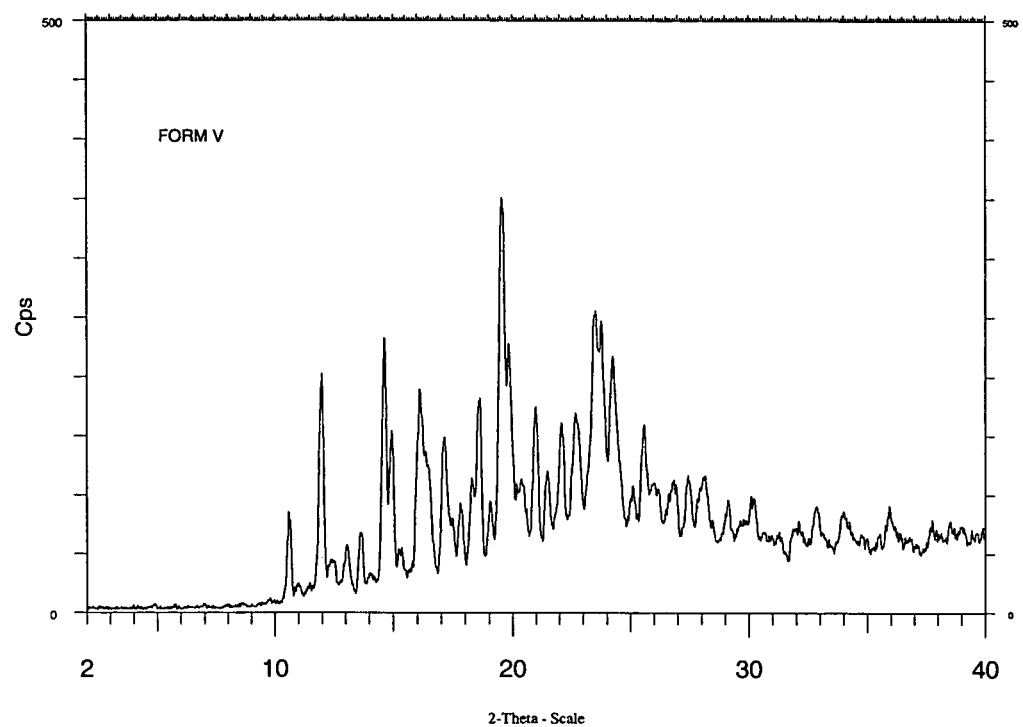
FIG. 5a illustrates the PXRD patterns of Form V of eletriptan hemisulphate and FIG. 5b illustrates the DSC thermogram of Form V for eletriptan hemisulphate.

FORM V
PXRD See FIG. 5a
The characteristic peaks are:

| 2-Theta ° | Intensity % | 2-Theta ° | Intensity % | 2-Theta ° | Intensity % |
|---|---|---|---|---|---|
| 10.556 | 24 | 18.572 | 50.9 | 25.958 | 31.7 |
| 11.943 | 57.6 | 19.046 | 26.7 | 26.168 | 29.7 |
| 12.418 | 12.3 | 19.53 | 100 | 26.685 | 29.4 |
| 13.032 | 16 | 19.837 | 64.8 | 26.801 | 31.4 |
| 13.611 | 19 | 20.386 | 32.1 | 27.445 | 32.9 |
| 14.008 | 9.2 | 20.972 | 49.6 | 28.122 | 32.5 |
| 14.609 | 66.2 | 21.471 | 34.1 | 28.485 | 22.2 |
| 14.908 | 43.8 | 22.09 | 45.8 | 29.134 | 27 |
| 15.277 | 14.3 | 22.692 | 48.2 | 30.202 | 27.4 |
| 16.103 | 53.8 | 23.495 | 72.8 | 31.281 | 19.4 |
| 16.422 | 35.6 | 23.745 | 70.3 | 31.948 | 19.8 |
| 17.105 | 42.3 | 24.236 | 61.9 | 32.882 | 25.6 |
| 17.423 | 22.5 | 25.113 | 30.5 | 33.999 | 24.3 |
| 17.794 | 26.2 | 25.568 | 45.3 | 34.798 | 18.5 |
| 18.271 | 32.3 | | | | |

Figure 5B:
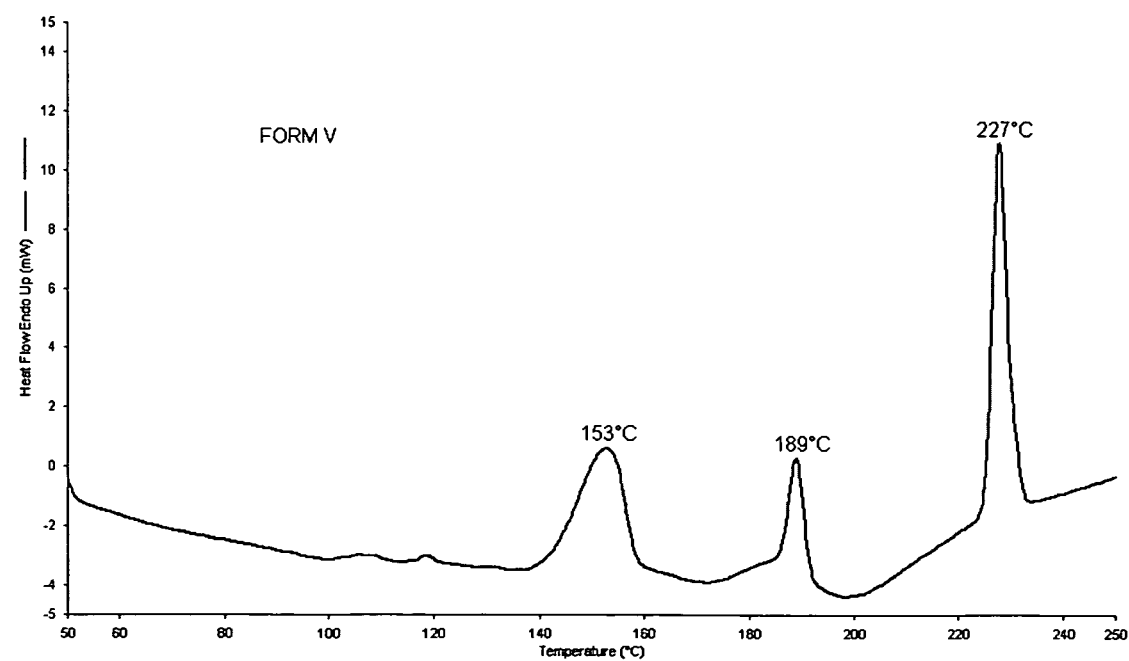

DSC See FIG. 5b (153° C., 189° C., 227° C., all endotherm).

Figure 6A:
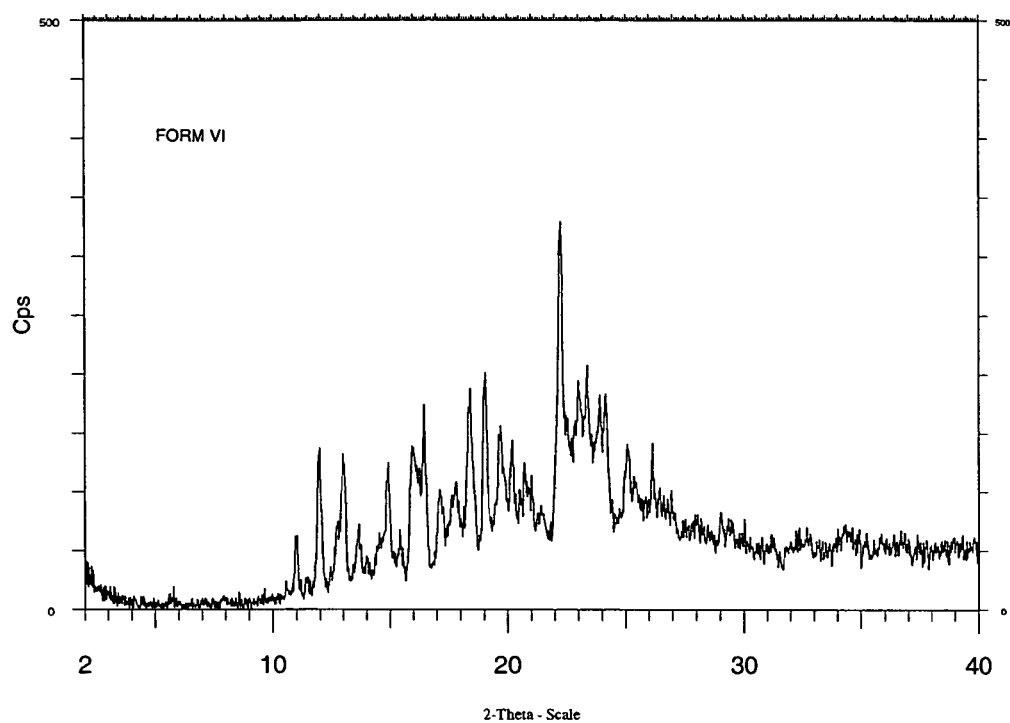
FIG. 6a illustrates the PXRD patterns of Form VI of eletriptan hemisulphate and FIG. 6b illustrates the DSC thermogram of Form VI for eletriptan hemisulphate.

FORM VI
PXRD See FIG. 6a
The characteristic peaks are:

| 2-Theta ° | Intensity % | 2-Theta ° | Intensity % | 2-Theta ° | Intensity % |
|---|---|---|---|---|---|
| 10.495 | 6.8 | 17.749 | 32.5 | 26.121 | 42.6 |
| 10.913 | 16.4 | 18.347 | 56.8 | 26.422 | 30.3 |
| 11.372 | 7.9 | 18.99 | 61 | 26.957 | 30.4 |
| 11.881 | 39.7 | 19.657 | 47.3 | 28.021 | 24.1 |
| 12.373 | 10.5 | 20.152 | 43.4 | 29.031 | 24.7 |
| 12.658 | 21.5 | 20.686 | 37.7 | 29.397 | 20.9 |
| 12.943 | 39.9 | 20.957 | 34.1 | 30.017 | 23 |
| 13.58 | 20.1 | 21.399 | 26.5 | 31.181 | 19 |
| 13.948 | 13.4 | 22.198 | 100 | 31.797 | 15.9 |
| 14.49 | 19.4 | 22.99 | 56.3 | 32.302 | 16.4 |
| 14.845 | 37.7 | 23.323 | 62.7 | 32.398 | 20.6 |
| 15.368 | 20.1 | 23.863 | 54.8 | 32.815 | 19.3 |
| 15.937 | 41.6 | 24.119 | 55.5 | 33.179 | 16.3 |
| 16.399 | 52.7 | 25.064 | 42.5 | 34.297 | 21.3 |
| 17.063 | 30.5 | 25.36 | 33.8 | 34.919 | 20.3 |

Figure 6B:
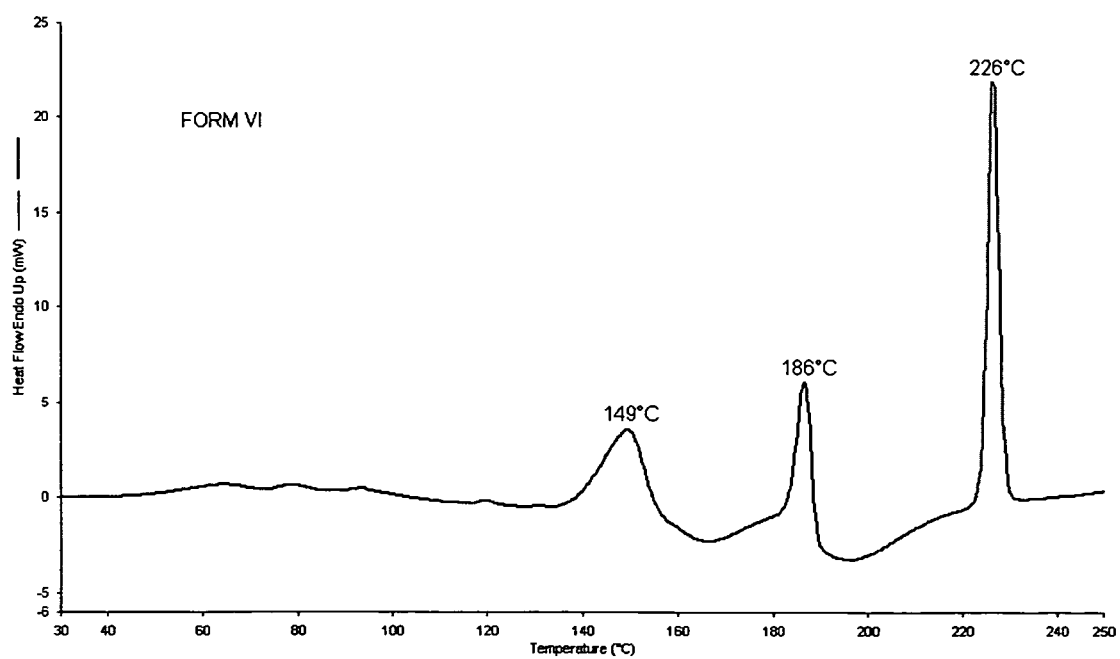

DSC See FIG. 6b (149° C., 186° C., 226° C., all endotherm).

Figure 7:
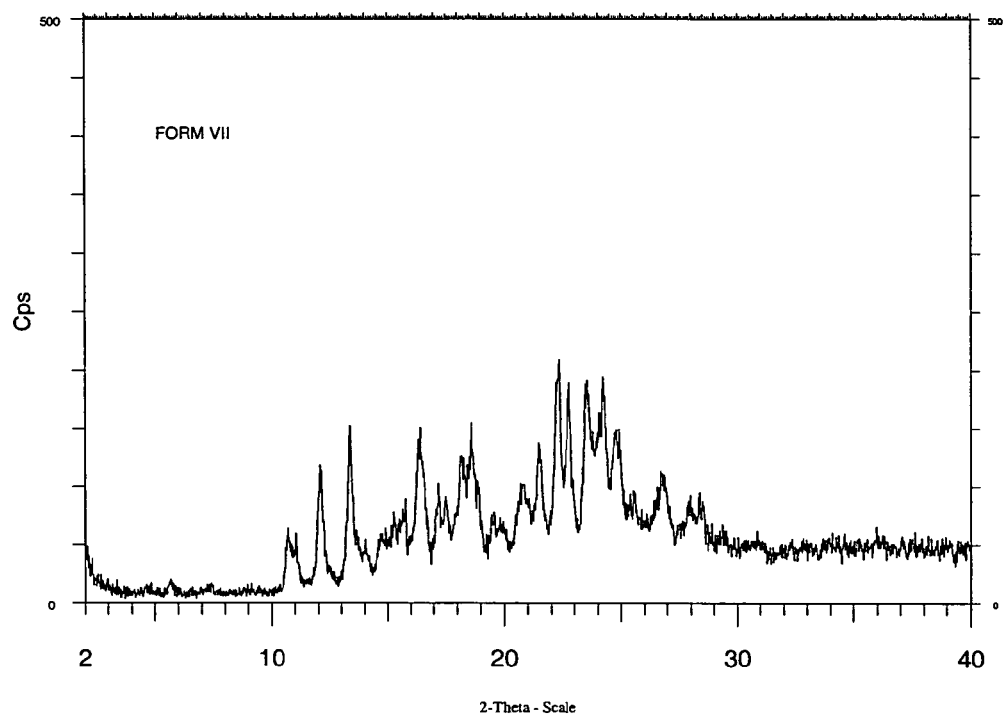
FIG. 7 illustrates the PXRD patterns of Form VII of eletriptan hemisulphate.

FORM VII
PXRD See FIG. 7
The characteristic peaks are:

| 2-Theta ° | Intensity % | 2-Theta ° | Intensity % | 2-Theta ° | Intensity % |
|---|---|---|---|---|---|
| 10.67 | 31.5 | 17.178 | 50.8 | 23.532 | 96 |
| 10.964 | 27.2 | 17.507 | 45.2 | 24.237 | 97.4 |
| 12.029 | 59 | 18.145 | 63.2 | 24.838 | 69.1 |
| 13.337 | 76.2 | 18.591 | 77.5 | 25.583 | 47.1 |
| 13.629 | 31.2 | 18.863 | 52.1 | 26.759 | 55.7 |
| 13.978 | 26.7 | 19.543 | 38.6 | 27.93 | 43.5 |
| 14.683 | 29.2 | 19.803 | 36.5 | 28.458 | 42.2 |
| 15.222 | 38.7 | 20.77 | 50.2 | 32.323 | 25.8 |
| 15.682 | 38 | 21.489 | 68.6 | 33.743 | 27.2 |
| 16.338 | 66.5 | 22.277 | 100 | 34.363 | 28.8 |
| 16.583 | 51.6 | 22.756 | 94.8 | | |

Figure 8:
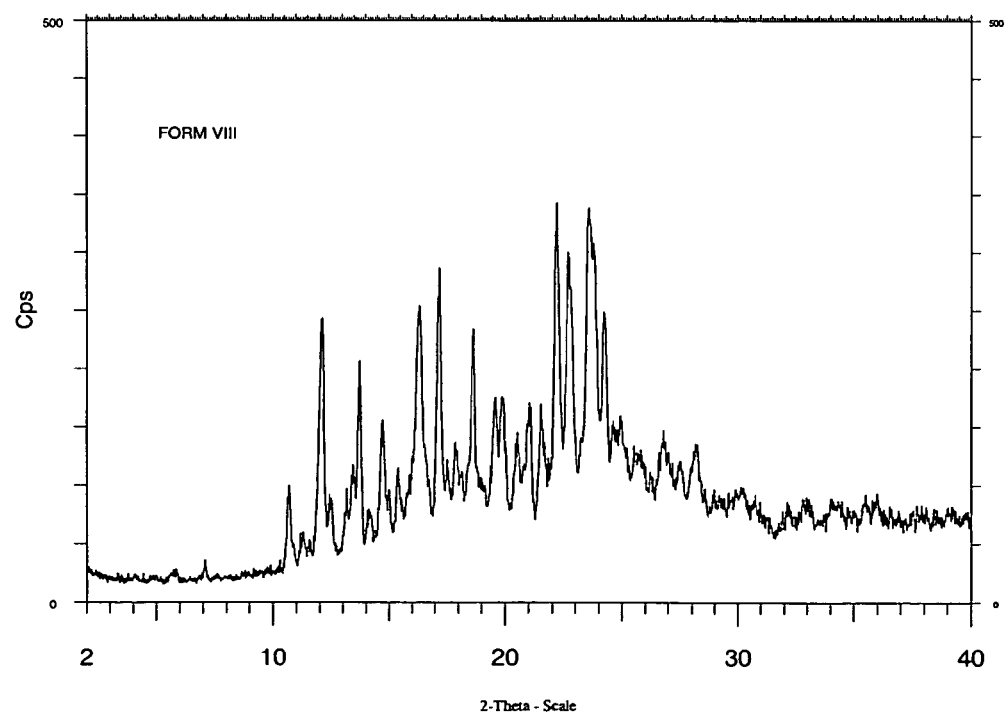
FIG. 8 illustrates the PXRD patterns of Form VIII of eletriptan hemisulphate.

FORM VIII
PXRD See FIG. 8
The characteristic peaks are:

| 2-Theta ° | Intensity % | 2-Theta ° | Intensity % | 2-Theta ° | Intensity % |
|---|---|---|---|---|---|
| 6.922 | 10.2 | 17.047 | 83.6 | 24.503 | 45.3 |
| 10.521 | 29.2 | 17.396 | 35.7 | 24.858 | 46.7 |
| 11.103 | 17.3 | 17.754 | 40.1 | 25.448 | 37.6 |
| 11.939 | 71.8 | 18.499 | 67.3 | 25.63 | 36.8 |
| 12.322 | 26.1 | 19.461 | 51.8 | 26.137 | 31.2 |
| 13.015 | 28.1 | 19.756 | 52 | 26.687 | 42.9 |
| 13.285 | 34.5 | 20.39 | 42.5 | 27.41 | 35.5 |
| 13.557 | 60.8 | 20.905 | 50.1 | 28.091 | 39.6 |
| 14.013 | 22.4 | 21.406 | 49.8 | 28.871 | 28 |
| 14.578 | 45.7 | 22.05 | 100 | 30.091 | 28.2 |
| 14.831 | 28.2 | 22.594 | 88.7 | 30.638 | 26.8 |
| 15.25 | 33.4 | 23.469 | 100 | 32.082 | 24.1 |
| 15.693 | 28.7 | 23.648 | 91.1 | 33.979 | 25.9 |
| 16.162 | 75.1 | 24.125 | 73.6 | 34.245 | 25.3 |

Figure 9:
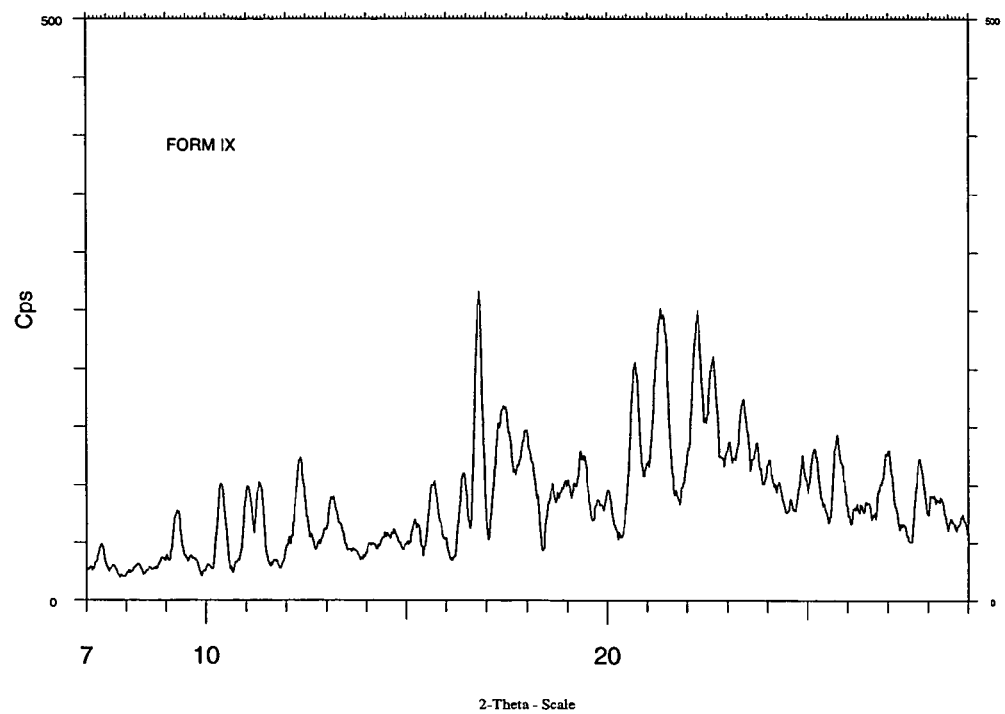
FIG. 9 illustrates the PXRD patterns of Form IX of eletriptan hemisulphate.

FORM IX
PXRD See FIG. 9
The characteristic peaks are:

| 2-Theta ° | Intensity % | 2-Theta ° | Intensity % | 2-Theta ° | Intensity % |
|---|---|---|---|---|---|
| 7.341 | 18.2 | 17.42 | 63 | 23.057 | 52.5 |
| 9.24 | 28.7 | 17.962 | 55 | 23.408 | 65.3 |
| 10.356 | 37.6 | 18.634 | 38.5 | 23.739 | 51.4 |
| 11.018 | 36.8 | 19.01 | 40.1 | 24.092 | 46.2 |
| 11.316 | 38.1 | 19.369 | 46.6 | 24.916 | 48 |
| 12.333 | 46.1 | 19.763 | 33.2 | 25.192 | 49.2 |
| 13.128 | 34 | 20.022 | 36.1 | 25.741 | 53.7 |
| 15.199 | 26.6 | 20.702 | 77.1 | 27.024 | 48.5 |
| 15.655 | 37.4 | 21.368 | 93.9 | 27.812 | 45.9 |
| 16.411 | 41.1 | 22.257 | 93.9 | 28.304 | 34.6 |
| 16.798 | 100 | 22.649 | 78.9 | 29.48 | 31.9 |

Figure 10:
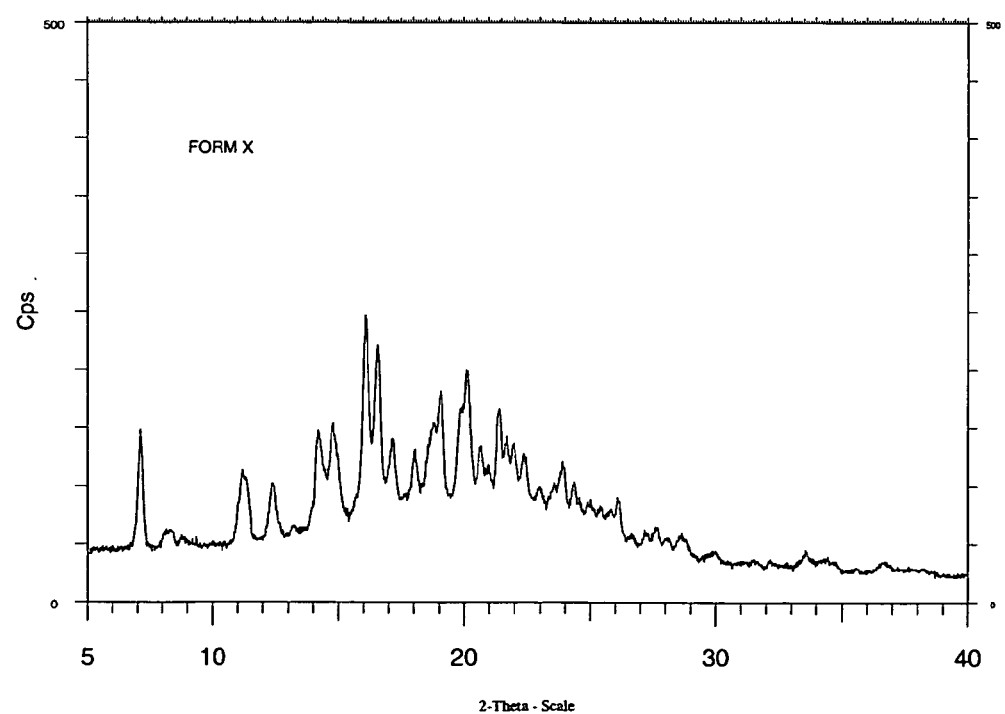
FIG. 10 illustrates the PXRD patterns of Form X of eletriptan hemisulphate.

FORM X
PXRD See FIG. 10
The characteristic peaks are:

| 2-Theta ° | Intensity % | 2-Theta ° | Intensity % | 2-Theta ° | Intensity % |
|---|---|---|---|---|---|
| 7.086 | 59.9 | 17.151 | 56.8 | 21.951 | 55.6 |
| 8.188 | 25.9 | 18.028 | 52.8 | 22.382 | 51.7 |
| 8.729 | 23.7 | 18.78 | 62.5 | 22.986 | 40.8 |
| 11.188 | 45.9 | 19.062 | 73.4 | 23.912 | 48.7 |
| 12.376 | 41.1 | 19.9 | 67.7 | 24.375 | 41.9 |
| 13.175 | 26.8 | 20.106 | 80.9 | 26.127 | 36.2 |
| 14.188 | 59.8 | 20.663 | 54.5 | 27.198 | 24.8 |
| 14.774 | 62.4 | 21.383 | 67.4 | 27.668 | 26.5 |
| 16.071 | 100 | 21.645 | 56.7 | 28.623 | 22.8 |
| 16.561 | 89.8 | | | | |

Figure 11:
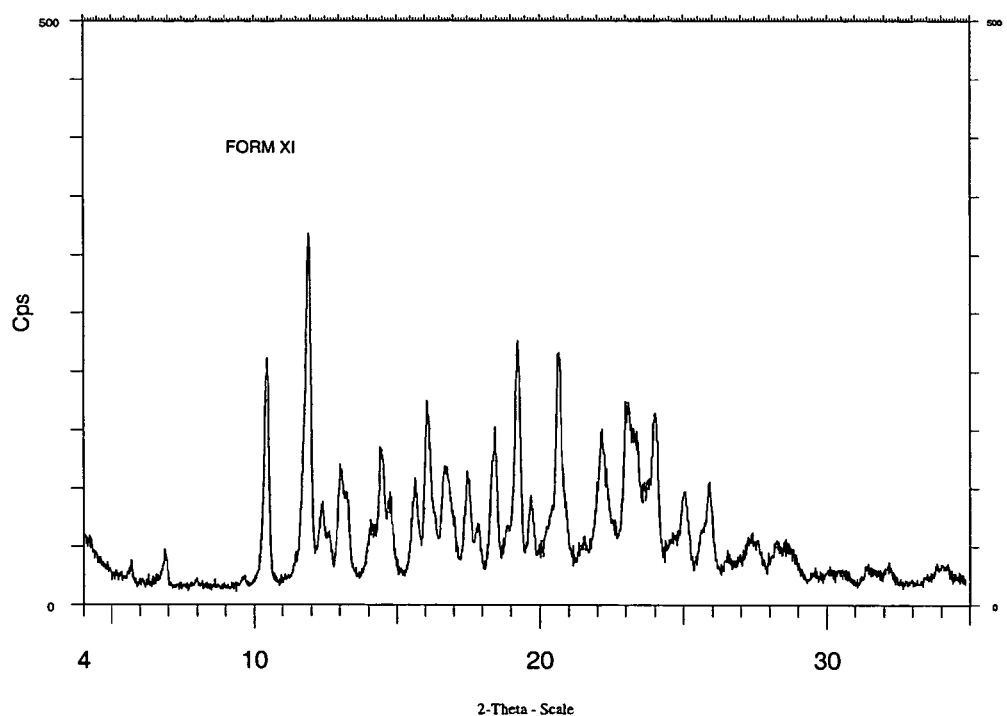
FIG. 11 illustrates the PXRD patterns of Form XI of eletriptan hemisulphate.

FORM XI
PXRD See FIG. 11
The characteristic peaks are:

| 2-Theta ° | Intensity % | 2-Theta ° | Intensity % | 2-Theta ° | Intensity % |
|---|---|---|---|---|---|
| 5.671 | 12.7 | 15.631 | 33.8 | 23.068 | 53.7 |
| 6.85 | 14.6 | 16.071 | 54 | 23.35 | 47.2 |
| 10.409 | 66.4 | 16.678 | 37 | 24.016 | 51.6 |
| 11.884 | 100 | 17.489 | 33.9 | 25.054 | 29.6 |
| 12.346 | 26.7 | 17.869 | 22.7 | 25.91 | 32.8 |
| 12.61 | 20 | 18.411 | 45.6 | 27.437 | 20 |
| 13.026 | 36.3 | 18.883 | 22.2 | 28.61 | 17.7 |
| 13.243 | 30.1 | 19.232 | 71.1 | 31.524 | 11.6 |
| 14.099 | 22.2 | 19.687 | 29.2 | 32.253 | 11.1 |
| 14.431 | 41.8 | 20.647 | 67.9 | 34.091 | 11.1 |

-continued

| 14.701 | 28.4 | 22.155 | 47.1 |
|---|---|---|---|

Figure 12A:
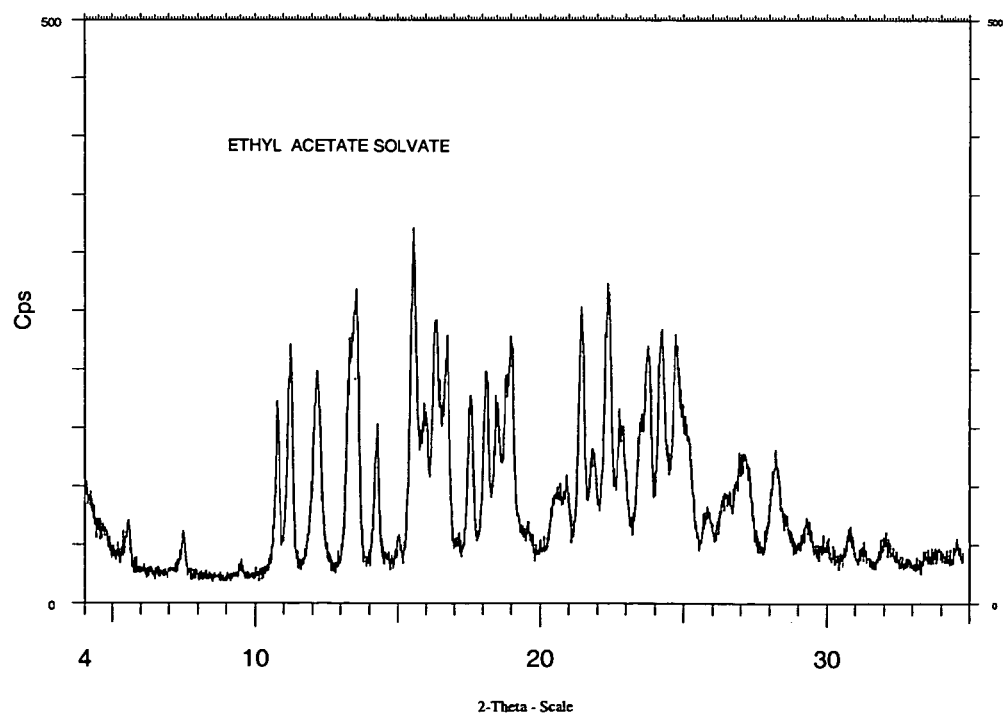
FIG. 12a illustrates the PXRD patterns of Form XII of eletriptan hemisulphate and FIG. 12b illustrates the DSC thermogram of Form XII for eletriptan hemisulphate.

FORM XII (EtOAc solvate 1)
PXRD See FIG. 12a
The characteristic peaks are:

| 2-Theta ° | Intensity % | 2-Theta ° | Intensity % | 2-Theta ° | Intensity % |
|---|---|---|---|---|---|
| 5.50 | 21.6 | 17.56 | 55.1 | 23.77 | 68.4 |
| 7.45 | 18.7 | 18.12 | 61.5 | 24.22 | 72.1 |
| 9.47 | 11.5 | 18.50 | 53.1 | 24.76 | 71.3 |
| 10.74 | 51.4 | 18.851 | 61.1 | 25.12 | 46.8 |
| 11.21 | 68.6 | 18.98 | 70.8 | 25.82 | 25.6 |
| 12.14 | 61.6 | 20.59 | 29.8 | 26.51 | 29.8 |
| 13.31 | 68.6 | 20.94 | 31.6 | 27.05 | 39.4 |
| 13.50 | 80.3 | 21.44 | 78.7 | 28.24 | 40.5 |
| 14.23 | 47.4 | 21.86 | 41.3 | 29.37 | 23.5 |
| 15.55 | 100 | 22.36 | 85 | 30.85 | 21.4 |
| 16.00 | 50.9 | 22.84 | 46.3 | 32.06 | 18.8 |
| 16.32 | 74.9 | 23.54 | 50.7 | 34.59 | 18 |
| 16.71 | 71.1 | | | | |

Figure 12B:
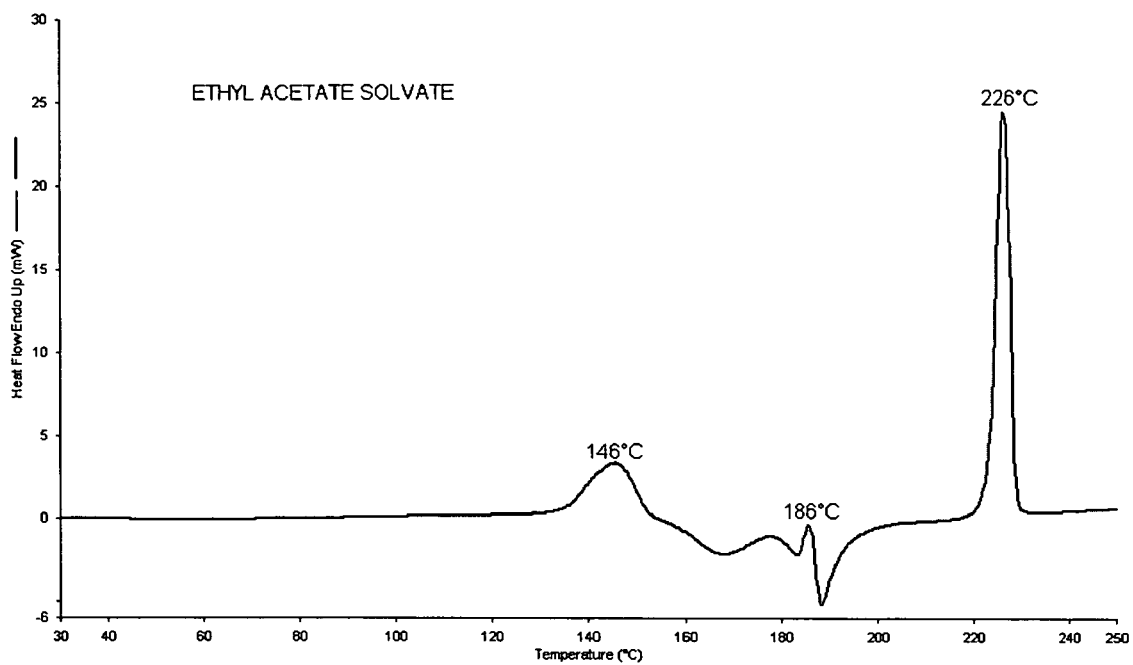

DSC See FIG. 12b (146° C., 186° C., 226° C., all endotherm).

Figure 13:
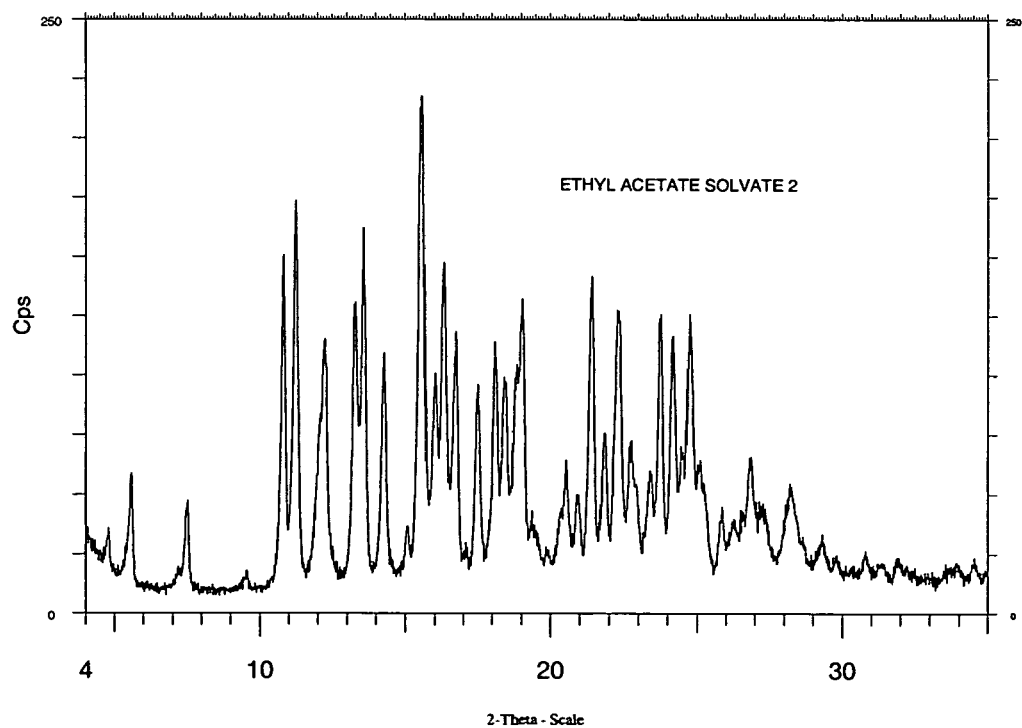
FIG. 13 illustrates the PXRD patterns of Form XIII of eletriptan hemisulphate.

FORM XIII (EtOAc solvate 2)
PXRD See FIG. 13
The characteristic peaks are:

| 2-Theta ° | Intensity % | 2-Theta ° | Intensity % | 2-Theta ° | Intensity % |
|---|---|---|---|---|---|
| 4.76 | 17.1 | 17.50 | 44.1 | 24.51 | 33.3 |
| 5.52 | 26.4 | 18.10 | 52.3 | 24.77 | 57.8 |
| 7.45 | 20.2 | 18.43 | 45.4 | 25.11 | 29.7 |
| 10.79 | 69.2 | 18.80 | 47.9 | 25.87 | 20.7 |
| 11.22 | 79.7 | 19.01 | 59.6 | 26.32 | 19.0 |
| 12.21 | 52.8 | 20.55 | 30.3 | 26.89 | 30.6 |
| 13.26 | 59.6 | 20.96 | 23.7 | 27.30 | 21.5 |
| 13.55 | 74.5 | 21.43 | 65.0 | 28.27 | 24.3 |
| 14.26 | 50.1 | 21.85 | 34.7 | 29.36 | 15.1 |
| 15.09 | 17.9 | 22.33 | 58.4 | 30.85 | 12.1 |
| 15.54 | 100 | 22.76 | 33.9 | 31.39 | 10.5 |
| 16.01 | 46.2 | 23.43 | 28.1 | 31.96 | 11.0 |
| 16.32 | 67.7 | 23.76 | 56.8 | 34.08 | 9.9 |
| 16.72 | 54.3 | 24.19 | 53.5 | 34.59 | 10.5 |

Figure 14:
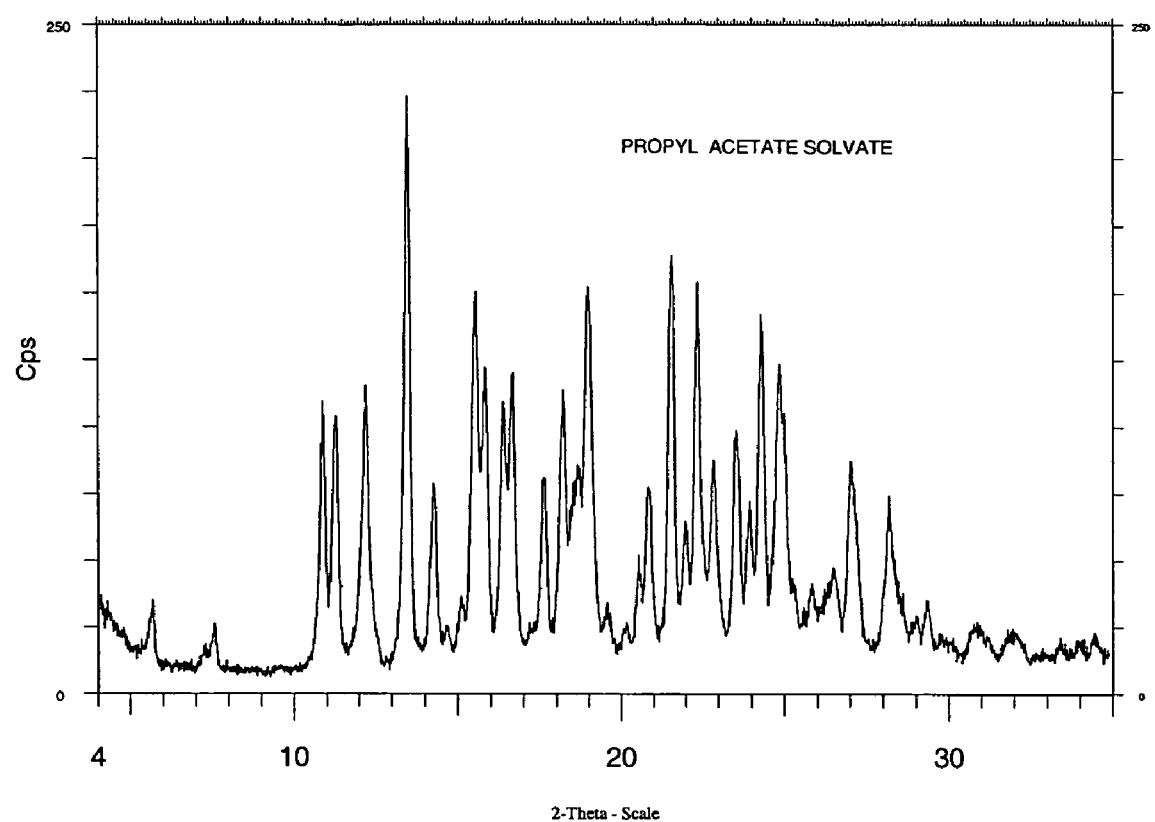
FIG. 14 illustrates the PXRD patterns of Form XIV of eletriptan hemisulphate.

FORM XIV (n-PrOAc solvate)
PXRD See FIG. 14
The characteristic peaks are:

| 2-Theta ° | Intensity % | 2-Theta ° | Intensity % | 2-Theta ° | Intensity % |
|---|---|---|---|---|---|
| 5.62 | 15.5 | 16.64 | 53.3 | 23.94 | 32.2 |
| 7.30 | 8.6 | 17.61 | 36.2 | 24.30 | 63.6 |
| 7.52 | 11.5 | 18.19 | 50.8 | 24.86 | 55.2 |
| 10.85 | 48.9 | 18.66 | 38.4 | 25.85 | 19.6 |
| 11.23 | 46.5 | 18.97 | 68.1 | 26.50 | 21.0 |
| 12.18 | 51.6 | 20.55 | 23.1 | 27.06 | 38.1 |
| 13.45 | 100 | 20.85 | 34.6 | 28.21 | 33.1 |
| 14.25 | 35.2 | 21.56 | 73.5 | 29.06 | 13.4 |
| 15.10 | 17.4 | 21.99 | 28.9 | 29.37 | 15.5 |
| 15.53 | 67.3 | 22.35 | 68.9 | 30.90 | 12.1 |
| 15.82 | 54.6 | 22.86 | 39.1 | 31.97 | 11.3 |
| 16.39 | 48.8 | 23.56 | 44.0 | | |

Forms III, V, VI and XI interchange, according to the prevailing relative humidity.

Eletriptan hemisulphate is usually prepared by the reaction of eletriptan free base with sulphuric acid. For instance, WO-A-01/23377 describes a process comprising the reaction of eletriptan with concentrated sulphuric acid as a refluxing solution in acetone or as a cooled solution in tetrahydrofuran. As a further aspect of the present invention, a new process for the preparation of eletriptan hemisulphate in a form particularly suitable for further processing to the form I polymorph has been developed.

In the new process, a cooled solution of eletriptan in acetone is treated with dilute aqueous sulphuric acid and the precipitated product is then recovered. The use of dilute sulphuric acid, in contrast to the use of concentrated sulphuric acid in the prior art process, is particularly advantageous since it is easier and safer to handle and leads to a cleaner reaction which produces lower levels of by-products.

The concentration of the solution of eletriptan in acetone is preferably from 7.5 to 15 liters per kg, most preferably about 10 liters per kg and the solution may advantageously be filtered prior to the addition of the dilute sulphuric acid. The use of from about 0.45 to 0.55 molar equivalents of sulphuric acid per mole of eletriptan produces optimal results and the dilute aqueous sulphuric acid preferably contains about 0.2 kg/liter of sulphuric acid. The reaction is preferably carried out at a temperature of from −5° C. to +5° C. and a gradual addition (for instance, over a period of 1 to 2 hours) of sulphuric acid is preferred. The product may conveniently be recovered by granulation (preferably at a temperature of from −5° C. to +5° C., over a period of about 2 hours), filtration, washing with further acetone (preferably two portions of approximately 0.5 liters per kg of product) and drying (preferably at about 50° C., in vacuo).

The product of this process, after drying, is typically a mixture of several hydrated, hygroscopic forms of variable water and acetone content (usually about 1.5 to 6% weight/weight water by Karl Fischer analysis). Forms III, V, VI, VIII and XI have been observed—see the experimental section below for details. Before conversion to the form I polymorph, using the process described above, the product is dried, if necessary, until its water content is no more than 6% weight/weight.

The following Examples illustrate the invention. Powder X-ray diffraction (PXRD) patterns were determined using a STOE STADI-P powder X-ray diffractometer. Each specimen was rotated whilst being irradiated with copper K-alpha$_1$ X-rays (wavelength=1.5406 Å). The analyses were performed with the goniometer running in transmission mode set for a 7 second count per 0.02° step over a two theta range of 4° to 56°. Only characteristic peaks are listed with relative intensity in brackets. Differential scanning calorimetry (DSC) was performed using a Mettler-Toledo DSC 822e instrument. The samples were heated at 10° C./minute over the range 30° C. to 300° C. Infra-red (IR) analysis was performed using a Bruker-Optics Vector 22 instrument. The sample was prepared using Golden-Gate ATR technology. Only characteristic peaks are listed.

EXAMPLE 1

A solution of eletriptan (100 g, 0.26 mol) in acetone (955 ml) was filtered and the filter was rinsed with further acetone (45 ml). The clear yellow solution obtained was cooled to 0° C. and dilute aqueous sulphuric acid (77 g of a 1:5 weight/weight mixture of 96% conc. sulphuric acid:water, 0.126 mol, 0.48 equivalents) was added with stirring, maintaining a temperature of from −5° C. to +5° C. The addition took place over a period of 1 hour. The resulting suspension was granulated by stirring for a further 2 hours at 0° C. The precipitate was recovered by filtration and washed with acetone (2×50 ml). After standing at ambient temperature for 2 hours, 10 g of the product (total weight 119.4 g), contaminated with water and acetone (water by K.F., 8.22%; acetone by GC ~1.85%), was removed for investigation.

DSC: 70° C. endo, 96° C. endo, 131° C. exo, 165° C. endo, 224° C. endo

PXRD: 5.6 (10), 6.79 (12), 10.33 (30), 11.83 (74), 12.21 (24), 13.15 (24), 13.57 (24), 14.55 (24), 15.61 (21), 16.01 (72), 16.57 (31), 23.43 (100)

IR: 3581, 3400–2200, 1710, 1479, 1295, 1138, 1037, 688, 597

Assigned as a mixture of form III and an acetone solvate.

The remaining amount was dried at 50° C. for 15 hours in a forced air dryer to yield eletriptan hemisulphate (100.2 g, 95%) as an off-white solid (water by K.F., 1.93%; acetone by GC, <0.04%).

DSC: 125° C. endo, 132° C. exo, 172° C. endo, 218° C. endo

PXRD: 5.67 (21), 6.85 (8), 7.83 (10), 10.4 (10), 10.88 (19), 11.37 (15), 11.89 (41), 12.61 (27), 12.91 (51), 13.63 (31), 14.85 (24), 15.89 (60), 16.39 (37), 17.07 (31), 17.65 (48), 18.29 (57), 22.15 (100)

IR: 3590, 3400–2200, 1480, 1293, 1139, 1024, 686, 598

Assigned as form VI.

A portion of this material (50.1 g) was further dried at 70° C. for 15 hours in a forced air dryer to yield 50.1 g of an off-white solid (water by K.F., 2.53%; acetone by GC, <0.01%).

DSC: 119° C. endo, 125° C. exo, 164° C. endo, 173° C. exo, 209° C. endo, 222° C. endo PXRD: 5.67 (21), 6.85 (8), 7.83 (10), 10.4 (10), 10.88 (19), 11.37 (15), 11.89 (41), 12.61 (27), 12.91 (51), 13.63 (31), 14.85 (24), 15.89 (60), 16.39 (37), 17.07 (31), 17.65 (48), 18.29 (57), 22.15 (100)

IR: 3590, 3400–2200, 1479, 1293, 1139, 1025, 686, 598

Assigned as a mixture of forms III and VI.

EXAMPLE 2

A solution of eletriptan (75 g, 196 mmol) in acetone (715 ml) was filtered and the filter was rinsed with further acetone (35 ml). The clear yellow solution obtained was cooled to 0° C. and dilute aqueous sulphuric acid (58 g of a 1:5 weight/weight mixture of 96% conc. sulphuric acid:water, 95 mmol, 0.47 equivalents) was added, with stirring, maintaining the temperature at from −5° C. to +5° C. The addition took place over a period of 45 minutes. The resulting suspension was granulated by stirring for a further 2 hours at 0° C. The precipitate was recovered by filtration, washed with acetone (2×35 ml) and dried at 50° C. for 16 hours in a forced air dryer to yield eletriptan hemisulphate (80.9 g, 94%) as a white solid (water by K.F., 1.43%; acetone by GC, 0.06%).

DSC: 129° C. endo, 135° C. exo, 171° C. endo, 182° C. exo, 221° C. endo

PXRD: 5.71 (19), 7.91 (6), 10.91 (20), 11.41 (8), 11.89 (31), 12.93 (87), 13.65 (13), 13.87 (10), 14.45 (15), 14.85 (23), 15.37 (16), 15.91 (51), 22.19 (100)

IR: 3590, 3400–2200, 1480, 1293, 1139, 1024, 686, 598

Assigned as form VI.

EXAMPLE 3

A solution of eletriptan (100 g, 0.26 mol) in acetone (955 ml) was filtered and the filter was rinsed with further acetone (45 ml). The clear yellow solution obtained was cooled to 0° C. and dilute aqueous sulphuric acid (77 g of a 1:5 weight/weight mixture of 96% conc. sulphuric acid:water, 0.126 mol, 0.48 equivalents) was added with stirring, maintaining the temperature at from −5° C. to +5° C. The addition took place over a period of 1 hour. The resulting suspension was granulated by stirring for another 2 hours at 0° C. The precipitate was recovered by filtration, washed with acetone (2×50 ml) and dried at 50° C. for 15 hours in a forced air dryer to yield eletriptan hemisulphate (111.5 g, 96%, 99.84% pure by HPLC) as an off-white solid (water by K.F., 2.94%; acetone by GC, 1.3%).

DSC: 116° C. endo, 120° C. exo, 150° C. exo, 179° C. endo, 223° C. endo

PXRD: 5.55 (52), 6.85 (43), 7.43 (25), 10.47 (27), 11.11 (22), 11.91 (73), 13.55 (53), 14.53 (25), 16.19 (94), 16.59 (26), 17.03 (53), 17.65 (48), 18.43 (54), 23.45 (100)

IR: 3591, 3400–2200,1710, 1480, 1302, 1138, 1024, 687, 600

Assigned as form VIII.

EXAMPLE 4

A solution of eletriptan (20 g, 52.3 mmol) in acetone (200 ml) was filtered. The resulting clear yellow solution was cooled to 0° C. and dilute aqueous sulphuric acid (15.1 g of a 1:5 weight/weight mixture of 96% conc. sulphuric acid: water, 24.6 mmol, 0.47 equivalents) was added with stirring, maintaining the temperature at from −5° C. to +5° C. The addition took place over a period of 2 hours. The resulting suspension was granulated by stirring for a further 2 hours at 0° C. The precipitate was recovered by filtration and dried at 50° C. for 10 hours in a forced air dryer to yield eletriptan hemisulphate (22.1 g, 93%, 99.89% pure by HPLC) as an off-white solid (water by K.F., 5.04%).

PXRD: 5.67 (10), 6.77 (10), 10.24 (15), 11.87 (66), 13.07 (21), 13.57 (43), 14.49 (35), 16.07 (91), 17.53 (23), 18.27 (23), 23.43 (100)

Assigned as form III.

EXAMPLE 5

A solution of eletriptan (20 g, 52.3 mmol) in acetone (200 ml) was filtered. The resulting clear yellow solution was cooled to 0° C. and dilute sulphuric acid (18.5 g of a 1:5 weight/weight mixture of 96% conc. sulphuric acid:water, 30.2 mmol, 0.58 equivalents) was added with stirring at a temperature of from −5° C. to +5° C. The addition took place over a period of 2 hours. The resulting suspension was granulated by stirring for a further 2 hours at 0° C. The precipitate was recovered by filtration and dried at 50° C. for 10 hours in a forced air dryer to yield eletriptan hemisulphate (18.0 g, 77%, 99.89% pure by HPLC) as an off-white solid (water by K.F., 5.32%).

EXAMPLE 6

A solution of eletriptan (66.3 g, 166 mmol) in acetone (633 ml) was filtered and the filter was rinsed with further acetone (30 ml). The resulting clear yellow solution was cooled to 0° C. and dilute aqueous sulphuric acid (51 g of a 1:5 weight/weight mixture of 96% conc. sulphuric acid: water, 83 mmol, 0.5 equivalents) was added, with stirring, at a temperature of from at −5° C. to +5° C. The addition took place over a period of 55 minutes. The resulting suspension was granulated by stirred for a further 3 hours at 0° C. After standing overnight at ambient temperature, the precipitate was recovered by filtration, washed with acetone (2×33 ml) and dried at 50° C. for 7 hours in a forced air dryer to yield eletriptan hemisulphate (70.5 g, 94%) as a white solid (water by K.F., 2.6%; acetone by GC, <0.01%).

DSC: 121° C. endo, 126° C. exo, 167° C. endo

PXRD: 5.67 (10), 6.77 (10), 10.24 (15), 11.87 (66), 13.07 (21), 13.57 (43), 14.49 (35), 16.07 (91), 17.53 (23), 18.27 (23), 23.43 (100)

IR: 3582, 3400–2200, 1479, 1302, 1151, 1036, 687, 601

Assigned as form III.

A sample of the product (10 g) was further dried at 70° C. for 3 hours to give a white solid (9.91 g, water by K.F., 1.99%).

DSC: 132° C. endo, 139° C. exo, 175° C. endo, 185° C. endo

PXRD: 5.69 (30), 6.8 (5), 7.86 (10), 10.89 (21), 11.85 (59), 12.57 (36), 12.89 (69), 15.89 (85), 17.47 (62), 18.29 (81), 18.95 (65), 22.13 (100)

IR: 3589, 3400–2200, 1480, 1304, 1149, 1037, 690, 620

Assigned as form VI.

EXAMPLE 7

A solution of eletriptan (100 g, 0.26 mol) in acetone (955 ml) was filtered and the filter was rinsed with further acetone (45 ml). The resulting clear yellow solution was cooled to 0° C. and dilute aqueous sulphuric acid (77 g of a 1:5 weight/weight mixture of 96% conc. sulphuric acid:water, 0.126 mol, 0.48 equivalents) was added with stirring at a temperature of from −5° C. to +5° C. The addition took place over a period of 55 min. The resulting suspension was granulated by stirring for a further 2 hours at 0° C. The precipitate was recovered by filtration, washed with acetone (2×50 ml) and dried at 50° C. for 14 hours in a forced air dryer to yield eletriptan hemisulphate (110.4 g, 96%, 99.86% pure by HPLC) as an off-white solid (water by K.F., 3.04%; acetone by GC, 0.01%).

DSC: 117° C. endo, 169° C. endo, 205° C. endo, 222° C. endo

PXRD: 5.65 (22), 6 (10), 10.28 (19), 10.49 (15), 11.89 (70), 12.93 (30), 13.57 (43), 14.55 (44), 16.13 (91), 17.07 (61), 17.53 (35), 18.35 (63), 23.47 (100)

IR: 3590, 3400–2200, 1479, 1302, 1138, 1025, 687, 589

Assigned as form III.

EXAMPLE 8

A suspension of eletriptan hemisulphate (hydrated form VI from Example 1, 10 g) in a mixture of ethyl acetate (100 ml) and water (1 ml) was heated under reflux, with stirring, for 16 hours (total water content ~1.2% volume/volume). A portion of the solvent (40 ml, 40% of the volume) was removed by azeotropic distillation and fresh, dry ethyl acetate (40 ml) was added. The suspension was heated under reflux for a further 6 hours. After cooling to ambient temperature, the precipitate was recovered by filtration, washed with ethyl acetate (10 ml) and dried at 70° C. for 7 hours to yield eletriptan hemisulphate form I polymorph (9.36 g, 94%) as a white solid.

DSC: 223° C. endo

IR: 3400–2200, 1480, 1302, 1133, 1006, 690, 603

EXAMPLE 9

A suspension of eletriptan hemisulphate (the hydrated product of Example 2, 10 g) in a mixture of ethyl acetate (100 ml) and water (1.5 ml) was heated under reflux, with stirring, for 16 hours (total water content ~1.65% volume/volume). A portion of the solvent (40 ml, 40% of the volume) was removed by azeotropic distillation and fresh, dry ethyl acetate (40 ml) was added. The suspension was heated under reflux for a further 6 hours. After cooling to ambient temperature (over 30 minutes), the precipitate was recovered by filtration, washed with ethyl acetate (10 ml) and dried at 70° C. for 3 hours to yield eletriptan hemisulphate form I polymorph (9.38 g, 94%) as an off-white solid.

DSC: 223° C. endo

IR: 3400–2200, 1480, 1302, 1133, 1006, 690, 603

EXAMPLE 10

A suspension of eletriptan hemisulphate (the hydrated form VIII product of Example 3, 2.5 g) in a mixture of ethyl acetate (25 ml) containing 1.7% volume/volume water was heated under reflux for 24 hours (total water content 2% volume/volume). A portion of the solvent (5 ml, 20% of the volume) was removed by azeotropic distillation. After cooling to ambient temperature, the precipitate was recovered by filtration, washed with ethyl acetate (2.5 ml) and dried at 70° C. for 4 hours to yield eletriptan hemisulphate form I polymorph (2.22 g, 93%) as a white solid.

DSC: 222° C. endo

EXAMPLE 11

A suspension of eletriptan hemisulphate (the hydrated form III product of Example 4, 5 g) in a mixture of ethyl acetate (50 ml) containing 0.45% volume/volume water was heated under reflux for 24 hours (total water content was 0.95% volume/volume). A portion of the solvent (10 ml, 20% of the volume) was removed by azeotropic distillation. After cooling to ambient temperature, the precipitate was recovered by filtration, washed with ethyl acetate (5 ml) and dried at 70° C. for 15 hours to yield eletriptan hemisulphate form I polymorph (4.7 g, 93%, 99.79% pure by HPLC) as a white solid.

DSC: 223° C. endo

EXAMPLE 12

A suspension of eletriptan hemisulphate (the product of Example 5, 5 g) in a ethyl acetate (50 ml) containing 0.45% volume/volume water was heated under reflux for 24 hours (total water content was 1% volume/volume). A portion of the solvent (10 ml, 20% of the volume) was removed by azeotropic distillation. After cooling to ambient temperature, the precipitate was recovered by filtration, washed with ethyl acetate (5 ml) and dried at 70° C. for 15 hours to yield eletriptan hemisulphate form I polymorph (4.7 g, 93%, 99.84% pure by HPLC) as a white solid.

DSC: 222° C. endo

PXRD: 7.37 (21), 9.27 (25), 10.37 (43), 11.35 (34), 12.35 (35), 16.81 (73), 17.47 (54), 17.93 (55), 18.67 (34), 19.43 (25), 21.39 (100)

EXAMPLE 13

A suspension of eletriptan hemisulphate (the hydrated forms III and V product of Example 6, 2.5 g) in ethyl acetate (25 ml) was heated under reflux for 4 hours (total water content was 0.26% volume/volume). After cooling to ambient temperature, the precipitate was recovered by filtration, washed with ethyl acetate (5 ml) and dried at 70° C. for 7 hours to yield eletriptan hemisulphate form I polymorph (2.1 g, 85%) as a white solid.

DSC: 222° C. endo

EXAMPLE 14

A suspension of eletriptan hemisulphate (the hydrated form VI product of Example 6, 2.5 g) in ethyl acetate (25 ml) was heated under reflux for 24 hours (total water content was 0.2% volume/volume). After cooling to ambient temperature, the precipitate was recovered by filtration, washed with ethyl acetate (5 ml) and dried at 70° C. for 7 hours to yield eletriptan hemisulphate form I polymorph (2.2 g, 89%) as a white solid.

EXAMPLE 15

A suspension of eletriptan hemisulphate (the hydrated form III product of Example 7, 2.5 g) in a mixture of ethyl acetate (25 ml) containing 0.3% volume/volume water was heated under reflux for 24 hours (total water content was 0.6% volume/volume). A portion of the solvent (5 ml, 20% of the volume) was removed by azeotropic distillation. After cooling to ambient temperature, the precipitate was recovered by filtration, washed with ethyl acetate (2.5 ml) and dried at 70° C. for 4 hours to yield eletriptan hemisulphate form I polymorph (2.1 g, 88%) as a white solid.
DSC: 223° C. endo

EXAMPLE 16

A suspension of eletriptan hemisulphate (with a high water content (~9%) and acetone content (~6.4%), 10 g) in a mixture of ethyl acetate (100 ml) and water (0.6 ml) was heated under reflux for 16 hours (total water content was about 1.5% volume/volume). A portion of the solvent (40 ml, 40% of the volume) was removed by azeotropic distillation and fresh, dry ethyl acetate (40 ml) was added. The reaction mixture was heated under reflux for a further 6 hours. After cooling to ambient temperature (over 30 minutes), the precipitate was recovered by filtration, washed with ethyl acetate (10 ml) and dried at 70° C. for 2.5 hours to yield eletriptan hemisulphate form I polymorph (8.2 g, 96%) as an off-white solid.
DSC: 223° C. endo

EXAMPLE 17

A suspension of eletriptan hemisulphate (with a water content of 5.23% and acetone content of less than 50 ppm, 10 g) in a mixture of ethyl acetate (100 ml) and water (1 ml) was heated under reflux for 16 hours (total water content was about 1.5% volume/volume). A portion of the solvent (40 ml, 40% of the volume) was removed by azeotropic distillation and fresh, dry ethyl acetate (40 ml) was added. The reaction mixture was heated under reflux for a further 6 hours. After cooling to ambient temperature (over 20 minutes), the precipitate was recovered by filtration, washed with ethyl acetate (10 ml) and dried at 70° C. for 3 hours to yield eletriptan hemisulphate form I polymorph (9.1 g, 96%) as an off-white solid.
DSC: 222° C. endo

EXAMPLE 18

A suspension of eletriptan hemisulphate (mainly hydrated form VI, water content 2.33%, 10 g) in a mixture of ethyl acetate (100 ml) and water (1 ml) was heated under reflux for 16 hours (total water content was about 1.3% volume/volume). A portion of the solvent (40 ml, 40% of the volume) was removed by azeotropic distillation and fresh, dry ethyl acetate (40 ml) was added. The reaction mixture was heated under reflux for a further 6 hours. After cooling to ambient temperature (over 20 minutes), the precipitate was recovered by filtration, washed with ethyl acetate (10 ml) and dried at 70° C. to yield eletriptan hemisulphate form I polymorph (9 g, 92%) as an off-white solid.
DSC: 224° C. endo
IR: 3400–2200, 1480, 1302, 1133, 1006, 690, 604

The invention claimed is:

1. A process for preparing anhydrous eletriptan hemisulphate form I polymorph characterized by a powder X-ray diffraction pattern obtained using copper K-alpha$_1$ radiation ($\lambda$=0.15406 nm) which shows main peaks at 9.28, 10.38, 11.37, 12.40, 16.84, 17.46, 17.53, 17.78, 17.98, 19.48, 20.70, 21.29, 21.45, 22.21, 22.64, 23.08, 25.20 and 25.79, comprising the steps of (a) slurrying any other form of eletriptan hemisulphate in a solvent of the formula CH$_3$COOR, wherein R is a C$_1$–C$_6$ alkyl group; (b) adjusting the water content of the slurry, if necessary, to 3% volume/volume or less; (c) heating the slurry; (d) concentrating the reaction mixture by azeotropic distillation, if necessary, until the water content of the reaction mixture has fallen to below 1% volume/volume; and (e) recovering the product.

2. A process as claimed in claim 1 wherein the solvent is ethyl acetate or n-propyl acetate.

3. A process as claimed in claim 2 wherein the solvent is ethyl acetate.

4. A process as claimed in claim 1 wherein in step (b) the water content is adjusted to from 0.2 to 2% volume/volume.

5. A process as claimed in claim 4 wherein the water content is adjusted to from 1.3 to 2% volume/volume.

6. A process as claimed in claim 1 wherein in step (c) the slurry is heated at from 60 to 80° C.

7. A process as claimed in claim 3 wherein in step (c) the slurry is heated under reflux.

8. A process as claimed in claim 1 wherein in step (d) the water content is adjusted to below 0.3% volume/volume.

9. A process as claimed in claim 8 wherein step (d) is performed during the course of step (c) rather than following it.

10. A process as claimed in claim 1 wherein the starting material of eletriptan hemisulphate is prepared by reacting a solution of eletriptan in acetone with dilute aqueous sulphuric acid.

* * * * *